United States Patent [19]
Patel et al.

[11] Patent Number: 6,158,862
[45] Date of Patent: *Dec. 12, 2000

[54] METHOD OF REDUCING GLARE ASSOCIATED WITH MULTIFOCAL OPHTHALMIC LENSES

[75] Inventors: Anilbhai S. Patel, Arlington; William M. Graham, Fort Worth, both of Tex.

[73] Assignee: Alcon Laboratories, Inc.

[*] Notice: This patent issued on a continued prosecution application filed under 37 CFR 1.53(d), and is subject to the twenty year patent term provisions of 35 U.S.C. 154(a)(2).

[21] Appl. No.: 08/984,909

[22] Filed: Dec. 4, 1997

[51] Int. Cl.⁷ .................................. G02C 7/10; A61F 2/16
[52] U.S. Cl. ...................... 351/164; 623/6.17; 623/6.27; 623/6.6
[58] Field of Search ........................... 351/161–165, 351/160 H, 167, 168, 159, 44, 160 R; 623/6, 6.11, 6.17, 6.27–6.29, 6.56, 6.6

[56] References Cited

U.S. PATENT DOCUMENTS

| | | | |
|---|---|---|---|
| 609,982 | 8/1898 | Winchester | 604/240 |
| 1,012,700 | 12/1911 | Payne | 604/232 |
| 1,157,552 | 10/1915 | Kispert | 604/233 |
| 2,020,111 | 11/1935 | Eisele | 604/242 |
| 2,806,473 | 9/1957 | Lingley | 604/243 |
| 3,076,455 | 2/1963 | McConnaughey et al. | 604/232 |
| 3,583,399 | 6/1971 | Ritsky | 604/232 |
| 3,811,441 | 5/1974 | Sarnoff | 604/201 |
| 3,895,633 | 7/1975 | Bartner et al. | 604/192 |
| 4,112,945 | 9/1978 | Helixon et al. | 604/220 |
| 4,122,836 | 10/1978 | Burnett | 600/5 |
| 4,162,122 | 7/1979 | Cohen | 351/161 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,540,405 | 9/1985 | Miller et al. | 604/232 |
| 4,592,746 | 6/1986 | Ewalt et al. | 604/220 |
| 4,610,672 | 9/1986 | Burkholder et al. | 604/220 |
| 4,636,211 | 1/1987 | Nielsen et al. | 623/6 |
| 4,637,697 | 1/1987 | Freeman | 351/161 |
| 4,641,934 | 2/1987 | Freeman | 351/159 |
| 4,655,565 | 4/1987 | Freeman | 351/159 |
| 4,769,033 | 9/1988 | Nordan | 623/6 |
| 4,813,955 | 3/1989 | Achatz et al. | 623/6 |
| 4,881,805 | 11/1989 | Cohen | 351/161 |
| 4,917,681 | 4/1990 | Nordan | 623/6 |
| 4,994,045 | 2/1991 | Ranford | 604/198 |
| 4,995,714 | 2/1991 | Cohen | 351/161 |
| 4,995,715 | 2/1991 | Cohen | 351/161 |
| 5,008,102 | 4/1991 | York | 351/161 |
| 5,017,000 | 5/1991 | Cohen | 351/161 |
| 5,019,099 | 5/1991 | Nordan | 623/6 |
| 5,054,905 | 10/1991 | Cohen | 351/161 |

(List continued on next page.)

FOREIGN PATENT DOCUMENTS

| | | |
|---|---|---|
| 0359 829 B1 | 11/1993 | European Pat. Off. . |
| 0 756 183 A2 | 1/1997 | European Pat. Off. . |
| WO 95/31156 | 11/1995 | WIPO . |

OTHER PUBLICATIONS

Zigman, "Tinting of Intraocular Lens Implants," *Arch Opthalmol*, vol. 100, 998 (1982).

Hovis, et al., "Physical Characteristics and Perceptual Effects of Blue–Blocking Lenses," *Optometry & Vision Science*, vol. 66(10), 682–689 (1989).

Guthrie, "Polymeric Colorants" *Rev. Prog. Color Relat. Topics*, vol. 20, 40–52 (1990).

Derwent Abstract—XP–02094520 (JP 05 045610A),May, 1991.

Derwent Abstract—XP–002094521 (JP 02 254402A), Mar., 1989.

Patent Abstracts of Japan—JP –6 324293 A, Nov., 1994.

*Primary Examiner*—Georgia Epps
*Assistant Examiner*—Jordan M. Schwartz
*Attorney, Agent, or Firm*—Jeffrey S. Schira

[57] ABSTRACT

A multifocal ophthalmic lens having a dye or dyes that block the transmission of near UV and/or blue light.

1 Claim, 2 Drawing Sheets

U.S. PATENT DOCUMENTS

| | | | |
|---|---|---|---|
| 5,056,908 | 10/1991 | Cohen | 351/161 |
| 5,074,877 | 12/1991 | Nordan | 623/6 |
| 5,076,684 | 12/1991 | Simpson et al. | 351/168 |
| 5,089,024 | 2/1992 | Christie et al. | 623/6 |
| 5,112,351 | 5/1992 | Christie et al. | 623/6 |
| 5,116,111 | 5/1992 | Simpson et al. | 351/161 |
| 5,117,306 | 5/1992 | Cohen | 359/565 |
| 5,120,120 | 6/1992 | Cohen | 351/161 |
| 5,121,979 | 6/1992 | Cohen | 351/161 |
| 5,121,980 | 6/1992 | Cohen | 351/161 |
| 5,129,718 | 7/1992 | Futhey et al. | 351/161 |
| 5,139,519 | 8/1992 | Kalb | 623/6 |
| 5,144,483 | 9/1992 | Cohen | 359/565 |
| 5,147,393 | 9/1992 | Van Noy et al. | 623/6 |
| 5,152,787 | 10/1992 | Hamblen | 623/6 |
| 5,158,572 | 10/1992 | Nielsen | 623/6 |
| 5,178,636 | 1/1993 | Silberman | 623/6 |
| 5,187,207 | 2/1993 | Gallas | 351/160 H |
| 5,192,317 | 3/1993 | Kalb | 623/6 |
| 5,192,318 | 3/1993 | Schneider et al. | 623/6 |
| 5,217,489 | 6/1993 | Van Noy et al. | 623/6 |
| 5,236,452 | 8/1993 | Nordan | 623/6 |
| 5,326,348 | 7/1994 | Nordan | 623/6 |
| 5,366,500 | 11/1994 | Schneider et al. | 623/6 |
| 5,381,193 | 1/1995 | Wedding | 351/163 |
| 5,419,775 | 5/1995 | Haffner et al. | 604/227 |
| 5,470,932 | 11/1995 | Jinkerson | 526/312 |
| 5,507,806 | 4/1996 | Blake | 623/6 |
| 5,617,154 | 4/1997 | Hoffman | 351/162 |
| 5,662,707 | 9/1997 | Jinkerson | 623/6 |
| 5,757,459 | 5/1998 | Bhalakia et al. | 351/164 |
| 5,846,457 | 12/1998 | Hoffman | 264/2.1 |
| 5,851,328 | 12/1998 | Kohan | 351/166 |
| 5,968,094 | 10/1999 | Werblin et al. | 623/6 |

METHOD OF REDUCING GLARE ASSOCIATED WITH MULTIFOCAL OPHTHALMIC LENSES

BACKGROUND OF THE INVENTION

This invention relates generally to the field of ophthalmic lenses and, more particularly, to bifocal, varifocal or multifocal intraocular lenses (IOLs).

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens. When age or disease causes the lens to become less transparent, vision deteriorates due to an inadequate image or by the scattered and diminished light which can be transmitted to the retina. This deficiency in the lens of the eye is medically known as a cataract. An accepted treatment for this condition is surgical removal of the lens and replacement of the lens function by an IOL.

The majority of ophthalmic lenses, including IOLs, currently used are of a monofocal design, (i.e., having one fixed focal length). The focal length of the implanted IOL generally is chosen to optimize distance vision at 3 meters from the patient. Most patients receiving an IOL still require glasses for clear distance and near vision.

Various multifocal ophthalmic lens designs are currently under investigation and these designs generally fall into one of two categories, refractive lenses and diffractive lenses. Refractive lenses are more fully described in U.S. Pat. Nos. 5,147,393, 5,217,489 (Van Noy, et al.), U.S. Pat. No. 5,152,787 (Hamblen), U.S. Pat. No. 4,813,955 (Achatz, et al.), U.S. Pat. Nos. 5,089,024, 5,112,351 (Christie, et al.), U.S. Pat. Nos. 4,769,033, 4,917,68, 5,019,099, 5,074,877, 5,236,452, 5,326,348 (Nordan), 5,192,318, 5,366,500 (Schneider, et al.), U.S. Pat. Nos. 5,139,519, 5,192,317 (Kalb), U.S. Pat. No. 5,158,572 (Neilsen), U.S. Pat. No. 5,507,806 and PCT Publication No. WO 95/31156 (Blake) and U.S. Pat. No. 4.636,211 (Nielsen, et al.), the entire contents of which are incorporated herein by reference. Diffractive lenses use nearly periodic microscopic structures on the lens to diffract light into several directions simultaneously. This is similar to a diffraction grating and the multiple diffraction orders focus the light into various images corresponding to different focal lengths of the lens. Diffractive multifocal contact lenses and IOLs are more fully discussed in U.S. Pat. No. 5,178,636 (Silberman), U.S. Pat. Nos. 4,162,122, 4,210,391, 4,338,005, 4,340,283, 4,995,714, 4,995,715, 4,881,804, 4,881,805, 5,017,000, 5,054,905, 5,056,908, 5,120,120, 5,121,979, 5,121,980, 5,144,483, 5,117,306 (Cohen), U.S. Pat. Nos. 5,076,684, 5,116,111 (Simpson, et al.), U.S. Pat. No. 5,129,718 (Futhey, et al.) and U.S. Pat. Nos. 4,637,697, 4,641,934 and 4,655,565 (Freeman), the entire contents of which are incorporated herein by reference.

While a diffractive IOL may have a number of focal lengths, generally, IOLs with only two focal lengths (far and near) are the most common. As with any simultaneous vision multifocal lens, a defocused image (or images) is superimposed (on the retina) the focused component because of the second lens power, but the defocused image is rarely observed by the user, who concentrates on the image of interest. The defocused image acts as a veiling glare source and thus interferes and degrades the focused image. Under certain circumstances (for example, at night), the pupil diameter of the user can expand to 5 millimeters (mm) or more, and a discrete distant light source (e.g., automobile headlights or street lights) can appear to be surrounded by a "halo" or "rings". A significant component of the halo is caused by the light that is directed to the near image which becomes defocused at the retina. The visibility of the halo is affected by the diameter of the lens region directing light to the near image, the proportion of total energy directed to the near image, and the overall imaging aberrations of the eye.

In U.S. Pat. No. 4,881,805, Cohen suggests that the intensity of light traveling through a diffractive lens can be varied by reducing the echelette depth at the lens periphery, thus reducing glare (column 4, lines 63–68). Cohen further states that the zone boundary radii of the diffractive zones need to obey the formula:

$$R_m = \sqrt{2mwf}$$

where:
w=the wavelength of light
m=integer representing the $m^{th}$ zone
f=focal length of the $1^{st}$ order diffraction
Column 5, lines 17–31.

Cohen's theory states that the glare results from the depth of the steps at the diffractive zone boundaries may be more applicable to contact lenses than intraocular lenses. Contact lenses generally move on the eye and the grooves can become filled with debris. In addition, the additive power of the contact lenses generally is less than that of intraocular lenses, which puts the defocused image more in focus, and also the patient's natural residual accommodation may alter the visibility of glare or halos.

U.S. Pat. Nos. 5,470,932 and 5,662,707 (Jinkerson), the entire contents of which is incorporated herein by reference, discloses the use of yellow dyes in ophthalmic lenses to block or lower the intensity of near UV and blue light (between 300 nanometers and 500 nanometers) that passes through the lens. Near UV and blue light is believed to be hazardous to the retina, and including blue-blocking dyes in the IOL is believed to restore the retinal protection lost when the natural lens is removed. Prior to the present invention, there has been no recognition in the art of using near UV and blue light blocking dyes to reduce the glare and halos that can be associated with multifocal IOLs.

Accordingly, a need continues to exist for a multifocal IOL that minimizes glare or halos.

BRIEF SUMMARY OF THE INVENTION

The present invention improves upon the prior art by providing a multifocal ophthalmic lens having a dye or dyes that block the transmission of near UV and/or blue light.

Accordingly, one objective of the present invention is to provide a multifocal ophthalmic lens that reduces glare or halos.

Another objective of the present invention is to provide a multifocal ophthalmic lens containing a near UV and/or blue light blocking dye or dyes.

This and other advantages and objectives of the present invention will become apparent from the detailed description and claims that follow.

DETAILED DESCRIPTION OF THE INVENTION

Figure 1:
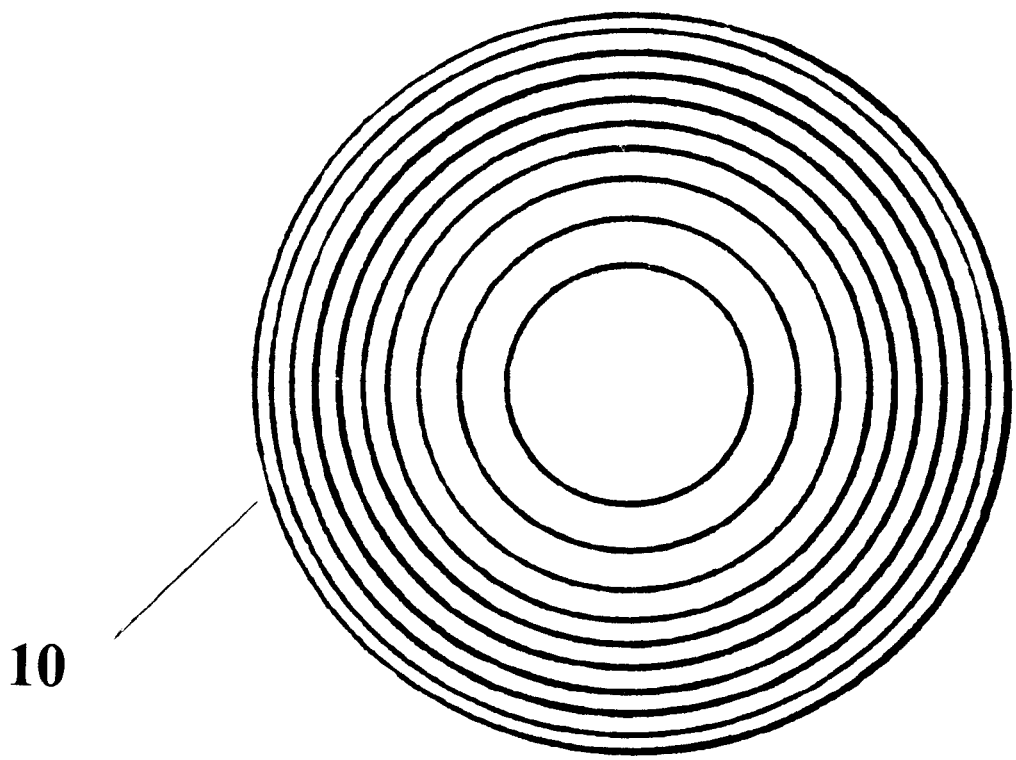
FIG. 1 is a plan view of a diffractive ophthalmic lens that may be used with the present invention.
Figure 2:
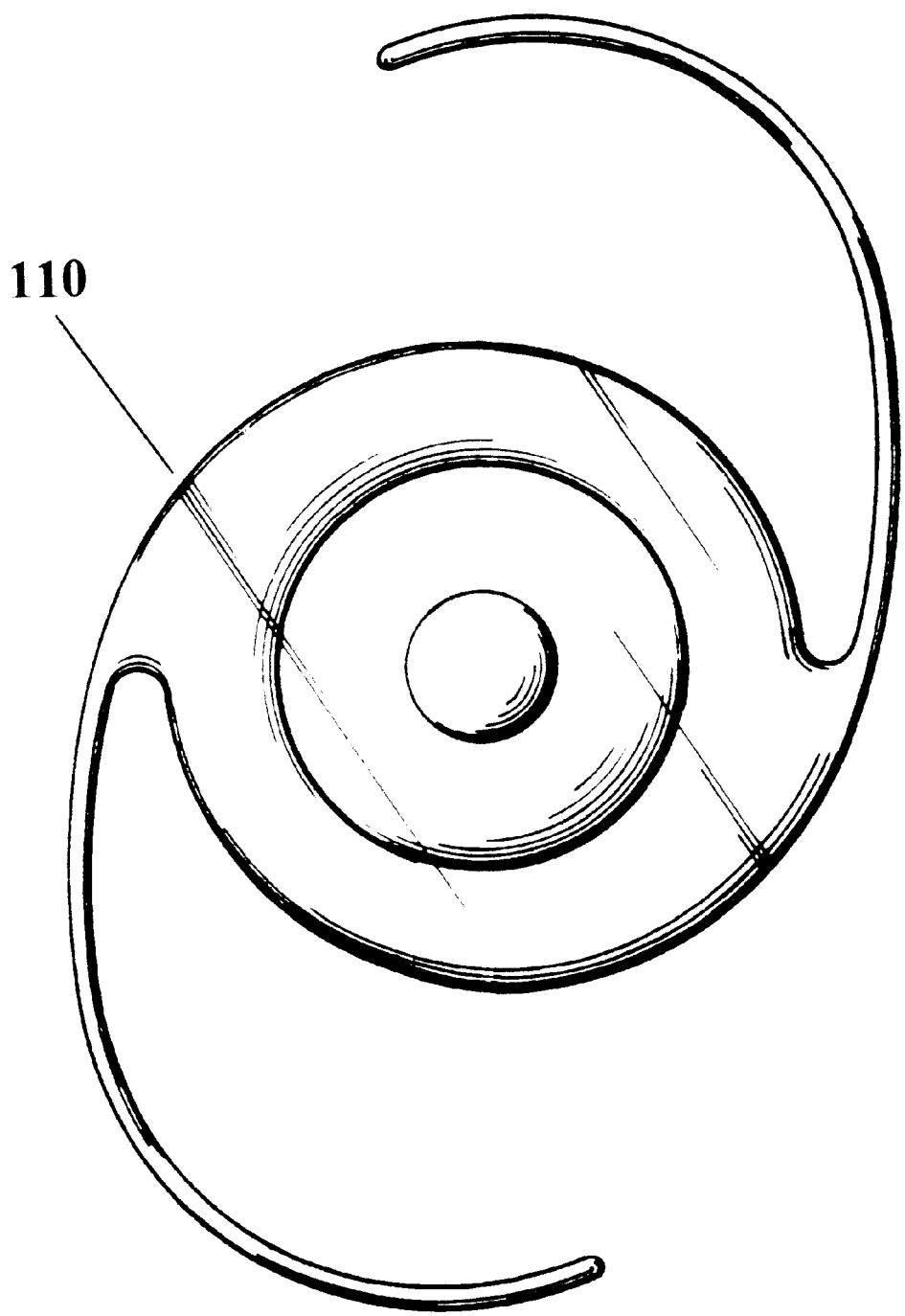
FIG. 2 is a plan view of a refractive ophthalmic lens that may be used with the present invention.

The inventors have discovered that including a near UV and/or blue light blocking dye or dyes in multifocal lens 10 or 110 reduces or eliminates the glare and halos associated with multifocal optics. One likely mechanism of action is that the Rayleigh scattering of light sources within the line of sight of the focused and defocused image by the cornea and the lens is disproportionate among the transmission band, with short wavelengths being scattered more than longer wavelengths (Rayleigh's Law holds that the scattering intensity is proportional to $\lambda^{-4}$ where $\lambda$ is the wavelength). Thus, the filtering of the shorter wavelengths reduces this scattering as well as reducing chromatic aberrations. One other mechanism is based on the recognition in the lighting industry that the discomfort associated with a glare source not in the line of sight may be predicted using the following equation:

$$\text{glare sensation} = (B_s^n / B_b^c) * (\omega^b / \rho^d)$$

where $B_s$ = luminace of the glare source $B_b$ = luminance of the background $\omega$ = angular subtense of the glare source $\rho$ = deviation of glare source from line of sight Constants n, b, c and d for predicting glare sensation caused by glare sources away from line of sight (e.g. headlights of automobiles in neighboring lanes or street lights) is not solidly established. Durrant (1977) established the values as n=1.6, b=0.8, c=1 and d=1.6. Using these values, a twenty-five percent reduction in the luminance for a lower wavelength of the glare source and background source luminance outside of the line of sight results in nearly a fifty-six percent reduction in glare sensation contributed by the lower wavelength.

All multifocal IOLs based on simultaneous vision optics have veiling, Rayleigh scattering law abiding, glare from out of focus images of light sources within the line of sight as well as glare effects of light sources not in the line of sight, especially during night driving when the pupil is large. The blue blocking and/or near UV blocking multifocal IOL of the present invention thus addresses both types of glare and improves upon the prior art by selectively filtering out the lower wavelengths from approximately 400 nanometers up to approximately 550 nanometers.

Any multifocal lens 10 or 110 can be used in the present invention and lens 10 or 110 may be made from any suitable material such as polymethylmethacrylate, silicone, soft acrylic or HEMA. Preferably, the blue-blocking dye used will be covalently bonded in the material used to make lens 10 or 110 and will be non-leaching. For example, if lens 10 or 110 is a soft acrylic lens, the dyes disclosed in U.S. Pat. Nos. 5,470,932 and 5,662,707 (Jinkerson) may be used.

This description is given for purposes of illustration and explanation. It will be apparent to those skilled in the relevant art that modifications may be made to the invention as herein described without departing from its scope or spirit. For example, the exact wavelengths that must be filtered out as well as the extent of the attenuation will vary by the lens material used. Therefore dyes that block out wavelengths below 410 nanometers, below 420 nanometers, below 430 nanometers, below 440 nanometers, below 450 nanometers, below 460 nanometers, below 470 nanometers, below 480 nanometers, below 490 nanometers, below 500 nanometers, below 510 nanometers, below 520 nanometers, below 530 nanometers, below 540 nanometers and below 550 nanometers may all be suitable for use with the present invention.

We claim:

1. A method of reducing the glare associated with a simultaneous vision multifocal ophthalmic lens implanted within an eye, comprising:

incorporating a non-leaching dye into a material used to make the multifocal ophthalmic lens, the dye suitable for selectively filtering out wavelengths of light between approximately 550 nanometers and approximately 400 nanometers from sources within a line of sight of the eye.

* * * * *